United States Patent [19]

Brazier

[11] Patent Number: 4,840,187
[45] Date of Patent: Jun. 20, 1989

[54] SHEATH APPLICATOR

[75] Inventor: Gary B. Brazier, Harwich, England

[73] Assignee: Bard Limited, Sunderland, England

[21] Appl. No.: 90,375

[22] Filed: Aug. 28, 1987

[30] Foreign Application Priority Data

Sep. 11, 1986 [GB] United Kingdom ............... 86 21884

[51] Int. Cl.⁴ .............................................. A61F 5/43
[52] U.S. Cl. .................................... 128/844; 604/349; 206/69
[58] Field of Search ............... 128/132 R, 138 R, 760, 128/842, 844, 885; 604/347, 349–353; 206/69

[56] References Cited

U.S. PATENT DOCUMENTS

| 2,456,507 | 12/1948 | Hendrickson et al. | |
|---|---|---|---|
| 2,567,926 | 9/1951 | Dunkelberger | |
| 2,715,903 | 8/1955 | Scholl | |
| 2,739,587 | 3/1956 | Scholl | |
| 3,703,892 | 12/1970 | Meyers | 206/69 |
| 4,239,044 | 12/1980 | Paulinch | 128/760 |
| 4,484,918 | 11/1984 | Omley | 604/349 |
| 4,540,409 | 9/1985 | Nystrom et al. | 604/349 |
| 4,668,229 | 5/1987 | Fago et al. | 604/349 |
| 4,690,678 | 9/1987 | Douglas-Hamilton | 604/349 |

FOREIGN PATENT DOCUMENTS

| 68712 | 1/1983 | European Pat. Off. | |
|---|---|---|---|
| 97521 | 1/1984 | European Pat. Off. | |
| 123661 | 10/1984 | European Pat. Off. | |
| WO8103609 | 12/1981 | PCT Int'l Appl. | |
| 8701582 | 3/1987 | PCT Int'l Appl. | 604/347 |
| 362584 | 11/1973 | Sweden | |
| 2001520 | 2/1979 | United Kingdom | |
| 2107194 | 4/1983 | United Kingdom | |
| 2120102 | 11/1983 | United Kingdom | 604/349 |
| 2185401 | 7/1987 | United Kingdom | 604/347 |

Primary Examiner—John D. Yasko
Assistant Examiner—Ralph Lewis
Attorney, Agent, or Firm—Dennison, Meserole, Pollack & Scheiner

[57] ABSTRACT

A sheath applicator assembly includes a tubular applicator casing, and a netting liner casing located in the applicator casing and secured to a closed end of the casing. A penile sheath is located inside the liner casing. The open end region of the casing is folded back over the casing, and the open end region of the sheath is folded back over the open end region of the casing.

18 Claims, 2 Drawing Sheets

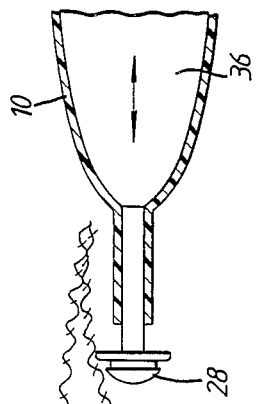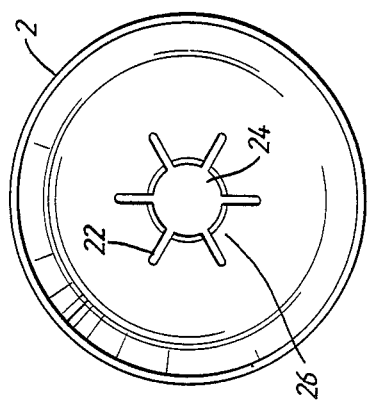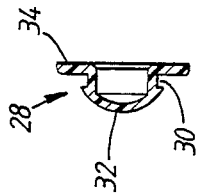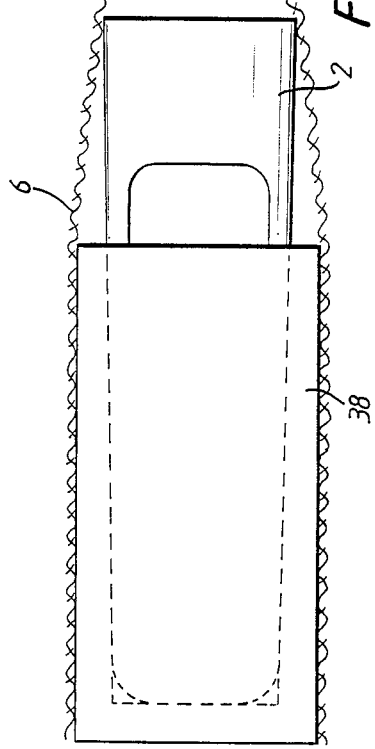

SHEATH APPLICATOR

The present invention relates to the application of a sheath to a penis.

In the specification the term "sheath" includes a penile sheath, a tubular device and a condom.

By "penile sheath" is meant a sheath which is fitted on to the penis to direct urine to a suitable receptacle such as a drainage bag. The sheath has a larger end adapted to be fitted over the penis, and a smaller end adapted to be connected to a tube leading to a collecting receptacle. The penile sheath is also sometimes referred to as a male external catheter.

By "tubular device" is meant a tube of substantially constant inner diameter having the same function as the penile sheath. The end of the tubular device remote from the penis can be coupled to a urine collecting receptacle. Alternatively, the remote end of the device can be tied up to enable urine to collect in the device. When convenient the device can then be untied and the urine discharged to a suitable receptacle.

Incontinent male patients may be catered for in a number of ways. One such way is to provide these patients with an incontinence device, i.e. a penile sheath, in hospitals, nursing homes or within the community. These devices are worn both by day and night, and are usually connected to a urine collection system to prevent unpleasant conditions occurring such as wetness, soreness, odour or infection.

One difficulty with the use of penile sheaths is that it is often embarrassing for the nurse, particularly a female nurse, to have to hold a patient's penis while applying the sheath for the treatment of incontinence.

It is extremely important that the penile sheath does not slip off the penis otherwise there would be a leakage of urine which may not be detected for some time, particularly when the sheath is worn at night.

Difficulty can arise in correctly fitting the penile sheath onto the penis so as to prevent the sheath from slipping off. These difficulties are enhanced by the elastic nature of the sheath which makes it difficult to fit.

It is an aim of the invention to alleviate the above difficulties, and in accordance with the invention there is provided a sheath applicator assembly comprising an applicator casing dimensioned to contain a sheath as hereinbefore defined, and to locate the sheath on a patient's penis, a flexible liner casing located in the applicator casing with an open end of the liner casing positioned at an open end of the applicator casing, and a sheath located in the liner casing with an open end at the open end of the liner casing, in which the open end region of the liner casing is folded back over the exterior of the open end region of the applicator casing, and the open end region of the sheath is folded back over the folded-back portion of the liner casing.

If the said sheath is a penile sheath, then the said larger end of the penile sheath is located at the open end of the liner casing.

In a preferred arrangement the liner casing may be secured to the applicator casing at a region remote from said open ends, and apertures may be located in the applicator casing to enable transversely spaced portions of the liner casing to be held.

A pressure-sensitive adhesive may be applied to the internal surface of the said open end of the sheath to facilitate its retention on a patient's penis. When the applicator assembly is stored ready for use, this adhesive coating is protected by a suitable release medium such as paper or coated plastic films.

The adhesive may be applied by any suitable technique such as for example by spraying, rolling or brushing. One particularly effective method of applying the adhesive is to wrap the sheath with a strip of adhesive tape; the tape having a backing to which the adhesive adheres less strongly than to the material of the sheath. The tape backing serves as a carrier for applying a band of pressure-sensitive adhesive to the folded-back internal surface of the sheath. In consequence the tape operates as a release strip which may be peeled away from the sheath to expose the adhesive coating thereon when the sheath is to be applied to a patient.

For a better understanding of the invention, embodiments of the invention will now be described by way of example with reference to the accompanying illustrative drawings, in which:

FIG. 6 is a side elevation in section of a component of the assembly of FIGS. 3 to 5;

FIG. 7 is a view of the closed left-hand end of the applicator casing of FIGS. 3 and 4; and FIG. 8 is a diagram illustrating the attachment of the liner casing to the applicator casing of the assembly of FIGS. 3 to 5.

Figure 1:
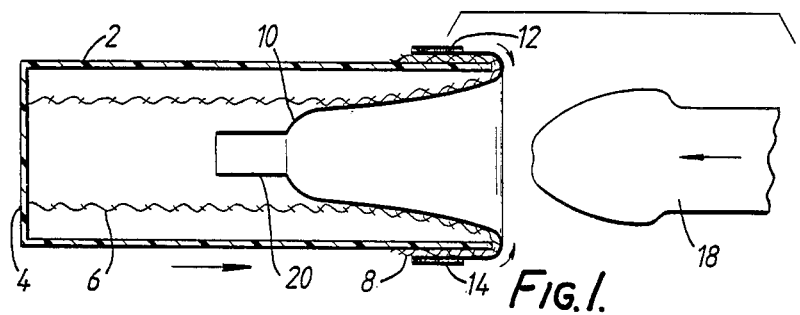
FIG. 1 is a side elevation in section of one sheath applicator assembly of the invention.
Figure 2:
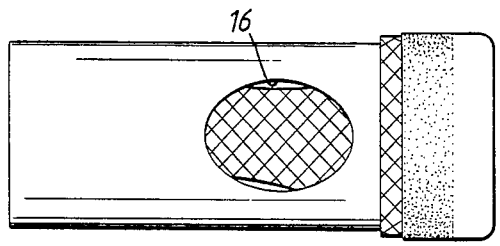
FIG. 2 is a side elevation of the assembly of FIG 1.

Referring to FIGS. 1 and 2 of the drawings, an applicator assembly of the invention includes a tubular applicator casing 2 which is closed at one end 4, the opposite end of the casing 2 being open. A flexible liner casing 6, shaped in the general form of a finger, is located in the applicator casing 2 and secured at one end to the closed end 4 of the applicator casing 2. This liner casing 6 is dimensioned so that its open end region 8 can project from the open end of the applicator casing 2.

A penile sheath 10 is located inside the liner casing 6 with the sheath larger end region 12 projecting from the applicator casing 2. The open end region 8 of the liner casing 6 is folded back over the open end region of the applicator casing 2, and the larger end region 12 of the sheath 10 is folded back over the open end region 8 of the liner casing 6. An adhesive coating is applied to the outer face of the folded back region of the sheath 10, and this adhesive coating is protected by a suitable release paper 14.

Two diametrically opposed apertures 16 are formed in the applicator casing 2 to enable the liner casing 6, the sheath 10 and the patient's penis to be gripped.

Referring to FIG. 1, it will be seen that the applicator casing 2 holds open the sheath 10 to receive the patient's penis 18. The sheath 10 includes a tubular end portion 20 to facilitate connection to a tube connector which will lead to a drainage bag.

In operation, the penis is thoroughly washed and dried, and the open end of the applicator casing 2 is guided on to the glans of the penis 18 which enters the held-open portion of the sheath 10. The penis glans, sheath 10 and the liner casing 6 are then lightly gripped with one hand through the apertures 16, and the release paper 14 is removed with the other hand. This light grip is maintained, and the applicator assembly is pushed towards the base of the penis thereby drawing the penis fully into the sheath 10, and unrolling the folded-back region of the liner casing 6 and the larger end region of the sheath 10 on to the rear part of the penis. It is this fitting of the larger end region of the sheath 10 on to the rear part of the penis which assists in providing the required secure mounting of the sheath 10 on the penis. This firm mounting is of course assisted by the adhesive coating. When the sheath 10 is fully fitted on to the penis, the applicator casing 2 and the liner casing 6 are withdrawn from the penis 10 by holding the applicator casing 2 through the apertures 16. The sheath 10 is then pressed lightly onto the penis to activate the adhesive.

Alternatively, the release paper 14 can be removed before the applicator casing 2 is applied to the penis.

In the illustrated embodiment the sheath larger end is held open and stretched so that its diameter is 130% of its normal unstretched diameter.

The applicator casing 2 can be made of any suitable material, for example a wood-pulp based material such as cardboard or a suitable plastics material such as polystyrene, polypropylene or polyethylene.

The liner casing 6 can be made of any suitable flexible material which will unfold easily to enable the sheath 10 to be applied over the penis 18. It is preferable, but not essential, that the material is of net-like construction. A preferred material is an extrudable stretched material such as polypropylene, nylon or polyethylene.

The sheath 10 may be made of any suitable elastomeric material such as latex, polyurethane, plasticised polyvinyl chloride, silicone rubber or a natural material such as pig's intestines.

The applicator casing 2 may have any suitable diameter to enable it to be advanced over the patient's penis. A suitable range of diameters is between 15 and 50 mm to enable the casing 2 to be used with a plurality of different sizes of sheath 10. A suitable length is 125 mm.

FIGS. 3 to 8 illustrate a second sheath applicator assembly of the invention which is similar in construction and operation to the assembly of FIGS. 1 and 2, and for clarity corresponding components of the two assemblies will be given the same reference numerals.

Referring to FIGS. 3 to 8 the assembly includes a tubular applicator casing 2 which is closed at one end 4, the opposite end of the casing 2 being open. This casing 2 is tapered slightly towards the closed end 4. A flexible liner casing 6, shaped in the general form of a finger, is located in the applicator casing 2 and secured at one end to the closed end 4 of the applicator casing 2. This liner casing 6 is made of a suitable netting material, and is dimensioned so that its open end region can project from the open end of the applicator casing 2.

To secure the closed end of the liner casing 6 to the closed end 4 of the applicator casing 2, six equally spaced slots 22 extend radially from a hole 24 extending through the center of the closed end 4. These slots 22 define six radially inwardly tapered tabs 26 in the closed end 4.

A stud 28 includes a stem 30 dimensioned to make an easy fit in the hole 24, a domed head 32 dimensioned to be pushed through the hole 24, and an annular flange 34 of greater diameter than the head 32.

A penile sheath 10 is located inside the liner casing 6 with the open end region of the liner casing 6 folded back over the open end region of the applicator casing 2, and the larger end region 12 of the sheath 10 folded back over the open end region of the liner casing 6.

Referring to FIG. 8, in one method of locating the liner casing 6 and the sheath 10 inside the applicator casing 2, the penile sheath 10 is located on a sheath mandrel 36 and the applicator casing 2 is located on a mounting tool 38 with the open end of the applicator casing 2 facing the sheath mandrel 36. The liner casing 6 is pulled over the applicator casing 2 with the closed end of the liner casing 6 at the right-hand end, and a stud 28 is mounted at the left-hand end of the sheath mandrel 36. The sheath mandrel 36 is advanced towards the applicator casing 2 causing the stud 28 to push the liner casing 6 into the applicator casing 2. This advancing movement continues until the stud head 32 has been pushed through the hole 24 in the casing end 4 so as to secure an end portion of the liner casing 6 to the centre portion of the casing end 4.

This advancement of the stud 28 also feeds the liner casing 6 into the applicator casing 2 so that the liner casing 6 is located in the applicator casing 2 with the open end region of the liner casing 6 folded back over the open end region of the applicator casing 2.

With the sheath mandrel 36 located in the applicator casing 2, the penile sheath 10 is separated from the mandrel 36 and the larger end region 12 of the sheath 10 is folded back over the open end region of the liner casing 6. The sheath mandrel 36 is then withdrawn from the applicator casing 2.

Two diametrically opposed apertures 16 are formed in the applicator casing 2 to enable the liner casing 6, the sheath 10 and the patient's penis to be gripped. These apertures 16 are rectangular with curved corners, and their dimensions have been chosen to facilitate the application of the sheath 10 onto the patient's penis.

A release strip 40 of tape has a backing to which is applied a pressure-sensitive adhesive which adheres thereto less strongly than to the material of the penile sheath 10. This tape backing serves as a carrier for applying a band of pressure-sensitive adhesive to the folded back region of the sheath 10 supported by the applicator tube 2.

The penis is thoroughly washed and dried and the open end of the applicator casing 2 is guided onto the glans of the penis which enters the held open portion of the sheath 10. The penis glans, sheath 10 and the liner casing 6 are then lightly gripped with one hand through the apertures 16, and the release strip 40 is pressed lightly so as to transfer the adhesive to the folded back region of the sheath 10. The release strip 40 is then peeled off the sheath 10 to expose the adhesive coating thereon. The light grip is maintained, and the applicator assembly is pushed towards the base of the penis thereby drawing the penis tip fully into the sheath 10 and unrolling the folded back region of the liner casing 6 and the larger end region of the sheath 10 onto the rear part of the penis. The sheath 10 is pressed gently around the penis to activate the adhesive, and the applicator casing 2 with the liner casing 6 is withdrawn.

The slight taper of the applicator casing 2 facilitates application of the casing to the penis and helps to retain the sheath 10 in position on the applicator casing 2. This taper also facilitates the moulding of the applicator casing 2.

Figure 3:
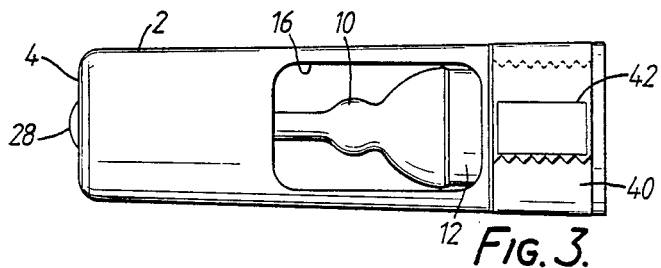
FIG. 3 is a side elevation of part of a second sheath applicator assembly of the invention.
Figure 4:
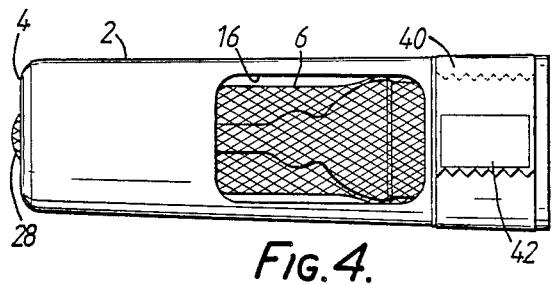
FIG. 4 is a side elevation of the complete assembly of FIG. 3.
Figure 5:
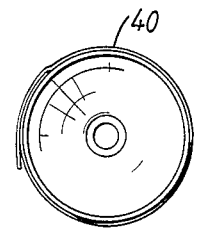
FIG. 5 is a view of the right-hand end of FIG. 4.

Referring to FIGS. 3 to 5, the release strip 40 extends slightly more than one turn around the applicator casing 2. A tag 42 can be adhered to the adhesive backing of the overlapping portion of the strip 40 so as to indicate the end portion of the strip 40. This tag 42 is then removed when the release strip 40 is removed. This tag 42 can contain relevant information on the sheath 10 together with any suitable advertising material.

If desired, the longitudinal edges of the backing of the release strip 40 can be uncoated with adhesive so as to facilitate removing the release strip 40 from the applicator casing 2, and also removing the sheath 10 after use.

The components of the applicator assembly of FIGS. 3 to 8 can be made of the same material and have the same dimensions as the corresponding components of the applicator assembly of FIGS. 1 and 2.

An important feature of the liner casing 6 is that the coefficient of friction between the liner casing 6 and the applicator casing 2 is less than the coefficient of friction between the penile sheath 10 and the liner casing 6. This ensures that when the applicator casing 2 is applied to the penis, the liner casing 6 unrolls from the applicator casing 2 so as to unroll the folded back region of the sheath 10 onto the patient's penis.

It is to be understood that any suitable number of apertures 16 can be formed in the applicator casing 2.

What is claimed is:

1. A sheath applicator assembly for locating a sheath on a patient's penis, comprising:
    a generally tubular applicator casing dimensioned to contain a sheath and having a first open end and a second end;
    a generally tubular flexible liner casing located in the applicator casing and having an open end positioned at the first end of said applicator casing, and folded back thereover, said liner casing being fixedly secured to said applicator casing at a region remote from the first end of said applicator casing; and
    a sheath located within said liner casing and having an open end at the open end of the liner casing and folded back over the open end of the liner casing and the applicator casing;
    the coefficient of friction between the liner casing and the applicator casing being less than the coefficient of friction between the liner casing and the sheath.

2. An assembly as claimed in claim 1 in which the liner casing is secured to said second end of the applicator casing.

3. An assembly as claimed in claim 2 in which the liner casing is secured to said second end portion by a stud which extends through a hole in the second end.

4. An assembly as claimed in claim 1 including a pressure-sensitive adhesive coating applied to the folded-back open end region of the sheath.

5. An assembly as claimed in claim 4 in which said adhesive coating is protected by a release medium.

6. An assembly as claimed in claim 6 including a strip of adhesive tape wrapped around the folded-back open end region of the sheath, in which the adhesive adheres less strongly to the strip than to the material of the sheath.

7. An assembly as claimed in claim 6 in which said strip extends more than 360° around the applicator casing, and comprising means adhered to an overlapping portion of said strip to indicate the end portion of said strip.

8. An assembly as claimed in claim 1 in which the liner casing is made of netting.

9. An assembly as claimed in claim 1 in which the liner casing is made of an extrudable stretched material.

10. An assembly as claimed in claim 9 in which the liner casing is made of a material such as polypropylene, nylon or polyethylene.

11. An assembly as claimed in claim 1 in which the applicator casing is made of a wood-pulp based material.

12. An assembly as claimed in claim 11 in which the applicator casing is made of cardboard.

13. An assembly as claimed in claim 1 in which the applicator casing is made of a plastics material.

14. An assembly as claimed in claim 13 in which the applicator casing is made of polystyrene, polypropylene or polyethylene.

15. An assembly as claimed in claim 1 in which the sheath is made of an elastomeric material.

16. An assembly as claimed in claim 15 in which the sheath is made of polyurethane, plasticised polyvinyl chloride, silicone rubber or a natural material.

17. An assembly as claimed in claim 16 in which the natural material is pigs' intestines.

18. An assembly as claimed in claim 1 wherein said applicator casing comprises a pair of diametrically opposed apertures which enable the liner casing and sheath to be gripped.

* * * * *